(12) United States Patent
Hung et al.

(10) Patent No.: US 7,327,273 B2
(45) Date of Patent: Feb. 5, 2008

(54) FLUID MONITORING DEVICE

(76) Inventors: Orlando R. Hung, 933 Greenwood Avenue, Halifax, NS (CA) B3H 3L1; Peter H. Gregson, 1168 South Park St., Halifax, NS (CA) B3H 2W8; David C. Roach, 212 1660 Hollis Street, Halifax, NS (CA) B3J 1V7

( * ) Notice: Subject to any disclaimer, the term of this patent is extended or adjusted under 35 U.S.C. 154(b) by 398 days.

(21) Appl. No.: 11/055,063

(22) Filed: Feb. 11, 2005

(65) Prior Publication Data
US 2006/0030822 A1    Feb. 9, 2006

Related U.S. Application Data

(60) Provisional application No. 60/543,552, filed on Feb. 12, 2004.

(51) Int. Cl.
*G08B 21/00* (2006.01)

(52) U.S. Cl. .................. 340/619; 340/918; 340/578; 340/583; 604/65; 604/66; 604/246; 604/253; 604/251

(58) Field of Classification Search ............... 340/619, 340/918, 578, 583; 604/246, 253, 251, 65, 604/66
See application file for complete search history.

(56) References Cited

U.S. PATENT DOCUMENTS

| | | | |
|---|---|---|---|
| 3,197,068 A | 7/1965 | Corbin et al. | |
| 3,655,095 A | 4/1972 | Kienitz | |
| 4,018,362 A | 4/1977 | Ubaud | |
| 4,137,940 A | 2/1979 | Faisandier | |
| 4,257,437 A | 3/1981 | Pearson | |
| 4,383,252 A | 5/1983 | Purcell et al. | |
| 4,493,710 A | 1/1985 | King et al. | |
| 4,496,346 A | 1/1985 | Mosteller | |
| 4,496,351 A | 1/1985 | Hillel et al. | |
| 4,498,901 A | 2/1985 | Finch | |
| 4,507,112 A | 3/1985 | Hillel et al. | |
| 4,533,350 A | 8/1985 | Danby et al. | |
| 4,623,331 A | 11/1986 | Cewers et al. | |

(Continued)

FOREIGN PATENT DOCUMENTS

WO    WO 99/42151    8/1999

OTHER PUBLICATIONS

Or Hung, MD. L Corneau MD; Incidence of Intra-Operative cessation of intravenous (IV) fluid administration, CJA 1998 45(511): A5.

(Continued)

*Primary Examiner*—Tai Nguyen

(57) ABSTRACT

This invention relates to a device to monitor the administration of a fluid through a conduit, such as intravenous fluid, and detect the completion of fluid delivery by monitoring the fluid level inside a chamber. The device will monitor, through an optical fluid sensor comprising a radiation source, two sensors, a logic means, and an indicating means, the bottom half of any "user supplied" drip chamber that is normally full during the administration of fluids. When the fluid level in the chamber drops below a predetermined level, the indicating means will initiate an electromechanical device that releases a pinching device to occlude the conduit. The pinching device is a rotary pincher that derives its force from a torsion spring and is held in the open position by the electromechanical device.

14 Claims, 4 Drawing Sheets

U.S. PATENT DOCUMENTS

| | | |
|---|---|---|
| 5,045,069 A | 9/1991 | Imparato |
| 5,139,482 A | 8/1992 | Simeon et al. |
| 5,439,442 A | 8/1995 | Bellifemine |
| 5,549,460 A | 8/1996 | O'Leary |
| 5,709,534 A | 1/1998 | O'Leary |
| 5,728,077 A | 3/1998 | Williams et al. |
| 5,741,121 A | 4/1998 | O'Leary |
| 5,800,386 A | 9/1998 | Bellifemine |
| 5,811,659 A | 9/1998 | Giebler |
| D402,365 S | 12/1998 | Lubitz |
| 5,938,643 A | 8/1999 | Lerner |
| D416,999 S | 11/1999 | Miyamoto |
| 6,083,206 A | 7/2000 | Molko |
| 6,234,773 B1 | 5/2001 | Hill et al. |
| 6,290,681 B1 * | 9/2001 | Brown ............... 604/246 |
| 6,337,631 B1 | 1/2002 | Pai et al. |
| 6,352,525 B1 | 3/2002 | Wakabayashi |
| 6,468,261 B1 * | 10/2002 | Small et al. ............ 604/535 |
| 6,491,659 B1 * | 12/2002 | Miyamoto ............. 604/30 |
| 6,736,801 B1 * | 5/2004 | Gallagher ............ 604/253 |
| 2003/0045840 A1 | 3/2003 | Burko et al. |
| 2003/0109836 A1 | 6/2003 | Ghekalim et al. |

OTHER PUBLICATIONS

M. Laskey AL, Dyer C, Tobias JD. Venous air embolism during home infusion therapy. Pediatrics. Jan. 2002; 109(1) :E15).

* cited by examiner

Vial Empty: Sensor 32 Receives More Light

Vial Full: Sensor 31 Receives More Light

FLUID MONITORING DEVICE

CROSS-REFERENCE TO RELATED APPLICATION

This application claims benefit of U.S. Provisional Patent Application Ser. No. 60/543,552, filed Feb. 12, 2004, entitled "FLUID MONITORING DEVICE", the contents of which are incorporated by reference.

FIELD OF THE INVENTION

This invention relates to a device to monitor the flow of a translucent fluid. In a preferred embodiment, the invention relates to a device to monitor administration of intravenous fluid.

DESCRIPTION OF THE PRIOR ART

Intravenous fluid is generally delivered to a patient by dripping it through an intravenous administration set with a drip chamber and tubing, using gravity. When the intravenous fluid container is empty, the drip chamber will run dry and the fluid flow will eventually be stopped. Three potential complications can occur if this termination of fluid delivery is not detected promptly:
(1) The back flow of the blood from the venous system of the patient will eventually cause clotting and obstruct further fluid delivery through the intravenous catheter. This demands the insertion of a new intravenous catheter into the patient's extremities, which is an invasive procedure and can be associated with complications, such as bleeding and infection.
(2) If the intravenous fluid is used as a carrier or vehicle for medications, such as intravenous anesthetics, completion of fluid delivery will also stop the administration of medications. With anesthetics, this lack of administration over time may mean that the patient can wake up from anesthesia during surgery and awareness can occur. With other types of medication, the administration dosages could suffer.
(3) Venous air embolism (VAE) can occur spontaneously due to mishaps with infusion fluid bags. Recently, Laskey et al. reported that VAE occurred when a bolus of air was unintentionally administered into a child venous system resulting in the immediate onset of respiratory and neurologic symptoms (Laskey A L, Dyer C, Tobias J D. Venous air embolism during home infusion therapy. Pediatrics. 2002 January; 109 (1):E15.). Patients will be particularly at risk of having a VAE when the infusion of fluid is under pressure for rapid fluid administration, such as patients in shock following trauma.

SUMMARY OF THE INVENTION

The present invention provides a fluid monitoring device, such as an intravenous monitor, and a method of monitoring administration of a fluid by detecting the presence of fluid in a chamber, such as a drip chamber, vial, or tube, using an optical fluid sensor device. The fluid monitoring device will indicate when the fluid level has dropped below a predetermined level inside the chamber. In such an event, optionally a pinch-off mechanism may occlude a conduit, for example an intravenous tube, connected either directly or indirectly to the chamber thereby preventing further flow of fluid. The pinch-off mechanism occludes the conduit distal to the optical fluid sensor device in the direction of fluid flow through the chamber.

This invention has particular importance in the prevention of venous air embolism, which is caused by the entrance of air into a patient's venous system through an intravenous bag.

According to one aspect of the present invention, there is provided an optical fluid sensor device for detecting presence of fluid in a chamber, comprising:

a radiation source;

a first sensor disposed so that the chamber is situated between the radiation source and the first sensor, and disposed to receive a majority of radiation emitted from the radiation source when the portion of the chamber through which the emitted radiation passes contains no fluid;

a second sensor disposed so that the chamber is situated between the radiation source and the second sensor, and disposed to receive a majority of radiation emitted from the radiation source when the portion of the chamber through which the emitted radiation passes contains fluid;

a logic means for controlling the radiation source, and for detecting as a first signal an amount of radiation falling on the first sensor, and for detecting as a second signal an amount of radiation falling on the second sensor, and for comparing the first and second signals; and means for indicating when no fluid is detected in the chamber.

Preferably, the radiation source is an infrared (IR) emitter and the means for indicating when no fluid is detected in the chamber is a visual and/or audible alarm. It is also preferable to use modulated or pulsed radiation to eliminate the interference caused by ambient light. When the radiation source is on, each sensor is read to determine the amount of emitted radiation reaching each sensor after passing through the chamber, but this reading also includes ambient light. By using modulated radiation, each sensor is read to determine the amount of ambient light reaching each sensor when the radiation source is off. The readings may then be corrected by removing the contribution due to ambient light. The corrected readings are compared to determine if fluid is present in the chamber.

The two-sensor system is advantageous since it allows for ratiometric and comparative measurements, thereby limiting the effects of inconsistent shape of the vial, variations in the refractive index of fluids, and ambient light.

According to another aspect of the present invention, there is provided a pinch-off mechanism for occluding a conduit, comprising:

a torsion spring;

means for loading the torsion spring having a rotary pincher and a pawl; and an electromechanical device having a lever engaging the pawl, whereby, when activated, the electromechanical device disengages the lever from the pawl of the loading means releasing stored energy in the torsion spring which rotates the rotary pincher thereby applying pressure against the conduit thereby occluding it.

A preferred use of the pinch-off mechanism is to occlude a conduit, such as a tube held in a narrow channel of an intravenous monitor. In one embodiment of said use, the means for loading or biasing the torsion spring is a thumbwheel. The thumbwheel is rotated to store energy in the torsion spring and to align a flattened surface of the rotary pincher with the side of the narrow channel to allow insertion of the tube. When the mechanism is activated, the electromechanical device disengages the lever from the pawl of the thumbwheel allowing rotation of the rotary pincher, thereby applying pressure against the tube in the narrow channel so as to occlude the tube. However, the pinch-off mechanism can be used with other flow systems where restriction of flow may be desired.

According to yet another aspect of the present invention, there is provided a fluid monitoring device, comprising:

(i) an optical fluid sensor device for detecting presence of fluid in a chamber, comprising:

a radiation source;

a first sensor disposed so that the chamber is situated between the radiation source and the first sensor, and disposed to receive a majority of radiation emitted from the radiation source when the portion of the chamber through which the emitted radiation passes contains no fluid;

a second sensor disposed so that the chamber is situated between the radiation source and the second sensor, and disposed to receive a majority of radiation emitted from the radiation source when the portion of the chamber through which the emitted radiation passes contains fluid;

a logic means for controlling the radiation source, and for detecting as a first signal an amount of radiation falling on the first sensor, and for detecting as a second signal an amount of radiation falling on the second sensor, and for comparing the first and second signals; and means for indicating when no fluid is detected in the chamber; and (ii) a pinch-off mechanism for occluding a conduit, comprising:

a torsion spring;

means for loading the torsion spring having a rotary pincher and a pawl, wherein the pincher is located in a position on the conduit distal to the optical fluid sensor device in the direction of fluid flow; and an electromechanical device having a lever engaging the pawl, whereby, the indicating means activates the electromechanical device thereby disengaging the lever from the pawl of the loading means releasing stored energy in the torsion spring which rotates the rotary pincher thereby applying pressure against the conduit thereby occluding it.

According to still another aspect of the present invention, there is a method for monitoring administration of a fluid using the fluid monitoring device as described herein, said method comprising:

activating the radiation source;

detecting radiation using the first sensor to produce a first signal and the second sensor to produce a second signal;

comparing the first signal to the second signal to detect the presence of fluid in the chamber; and activating the pinch-off mechanism to occlude the conduit when no fluid is present.

According to a preferred aspect of the present invention, there is provided a use of the optical fluid sensor device described herein for monitoring the flow of a fluid in an intravenous monitor. However, the optical fluid sensor device has many other applications wherein the flow of a translucent fluid is to be monitored, for example, the flow in a fuel line of a motorized vehicle.

There are a number of advantages flowing from the invention, namely:

1. A self-contained unit eliminating the complexity of parts and attachments to the intravenous administration set. It also eliminates protrusions, for example, wires that can become entangled when being attached to the chamber or when in use.
2. A pinch-off mechanism requiring the least amount of parts and a minimal amount of area. The rotary action of the pinch-off mechanism also delivers the maximum amount of force to the "pinching" action on the tube. It optimizes the force by transforming torque to lateral force at the pinch point, through the use of a moment arm. It has the potential of preventing a VAE from the infusion delivery system by the "pinching" mechanism of the device when the intravenous fluid bag is empty.
3. An optical fluid sensor using an infrared emitter and sensors to check for the presence of a fluid (for more detail see electronics section). This device checks for the presence of fluid and emits a signal when the fluid vial is empty.
4. A holding mechanism providing a tolerance fit that attaches to the stem of the I.V. drip chamber, (which is composed of a compressible material). This allows for a tight, non-slip, effective connection to the intravenous administration set. The advantage of this method is that, unlike other methods, it does not require any moving parts. This will result in reduced manufacturing costs (for instance, the example shown can be injection molded). However, other methods of attachment could be used, employing the same concept. These could include formed spring devices such as wire or metal strips, or rubber-like materials, which would have some compressive qualities. Any of these methods could also have serrated surfaces, which increase the holding capability.
5. A battery location and hookup providing several advantages. The battery may be a standard nine volts DC, which is mounted from the bottom of the device. First, it provides quick and easy access to changing the battery, since there is no cover to remove. Second, no cover means less surface area, saving additional size to the unit. Thirdly, having no battery cover means that there is one less piece to make, ultimately reducing the total cost of the unit. Alternatively, the battery may be a rechargeable battery that is integral to the device, inductively charged through the case.
6. An electronic design which is greatly simplified since the level of the fluid is picked up by the IR sensors in the fashion described above, thereby again reducing cost and size of the unit (for circuit design, see electronics section).
7. A visual and/or audible alarm ensuring timely attention to a situation before it becomes a problem. With reductions in nursing staff, each nurse has increased duties and responsibilities. If the attendant nurse is busy with another task, the alarm will alert her/him of the completion of fluid delivery.

BRIEF DESCRIPTION OF THE DRAWINGS

In order that the invention may be more clearly understood, a preferred embodiment thereof will now be described in detail by way of example, with reference to the accompanying drawings, in which.

DETAILED DESCRIPTION OF THE PREFERRED EMBODIMENT

Figures 1A, 1B:
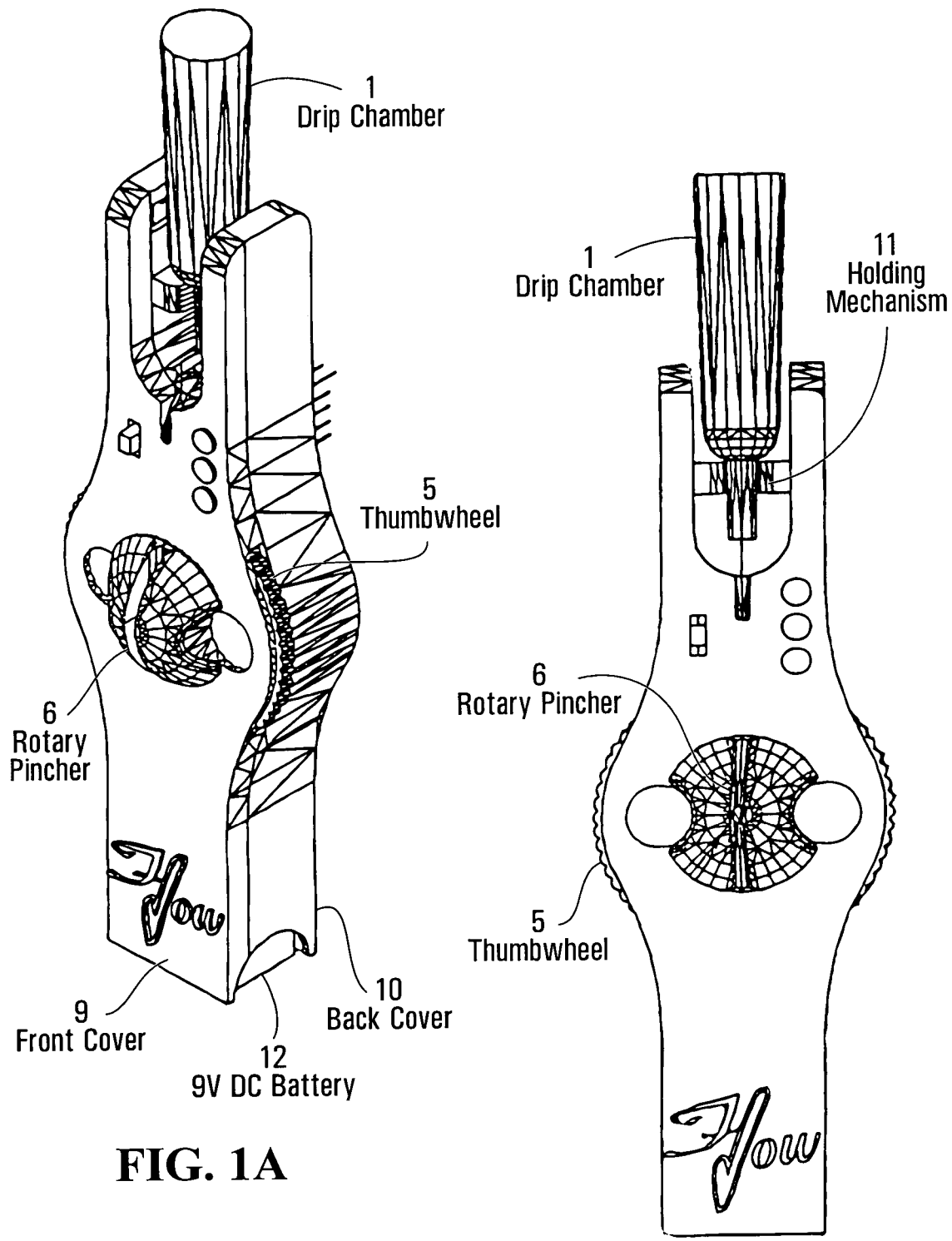
FIG. 1a and b are two assembly views of the device.

The following is a description of a preferred embodiment of the invention, embodied in an intravenous monitor. The device includes a drip chamber 1. The chamber is a conventional drip chamber found on most I.V. sets. An infrared emitter 2 and pick-up (sensor) is included as well. There is also a circuit board 3. An electromechanical device 4, preferably a solenoid, is included. Other components such as a thermo strip could be used instead of the solenoid depending on the reaction time required. A thumbwheel 5 is used to manually rotate the rotary pincher 6 to the open position. This motion loads a torsion spring (not shown) that supplies the force to the pincher. The rotary pincher is mounted on the thumbwheel and "pinches" the tube (stopping the flow) as it rotates 90 degrees counterclockwise. This occurs when the signal is received from the circuit board. A lever 7 is attached to the electromechanical device (EMD) and is used to increase the force of the EMD. This allows the selection of a smaller, more cost-effective EMD. The torsion spring (not shown) provides the force for "pinching-off" the tube. A front cover 9 provides protection to all internal components. As well, it provides a "slot" to insert the drip apparatus tubing. The slot locates the tube in a way that allows the pincher to effectively stop the fluid flow when it is in the closed position. A back cover 10 provides protection to all internal components and includes the holding mechanism that attaches the entire unit to the drip chamber. A holding mechanism 11 being a serrated compression fitting provides the means of attachment to the drip chamber.

The Electronics

Figure 2:
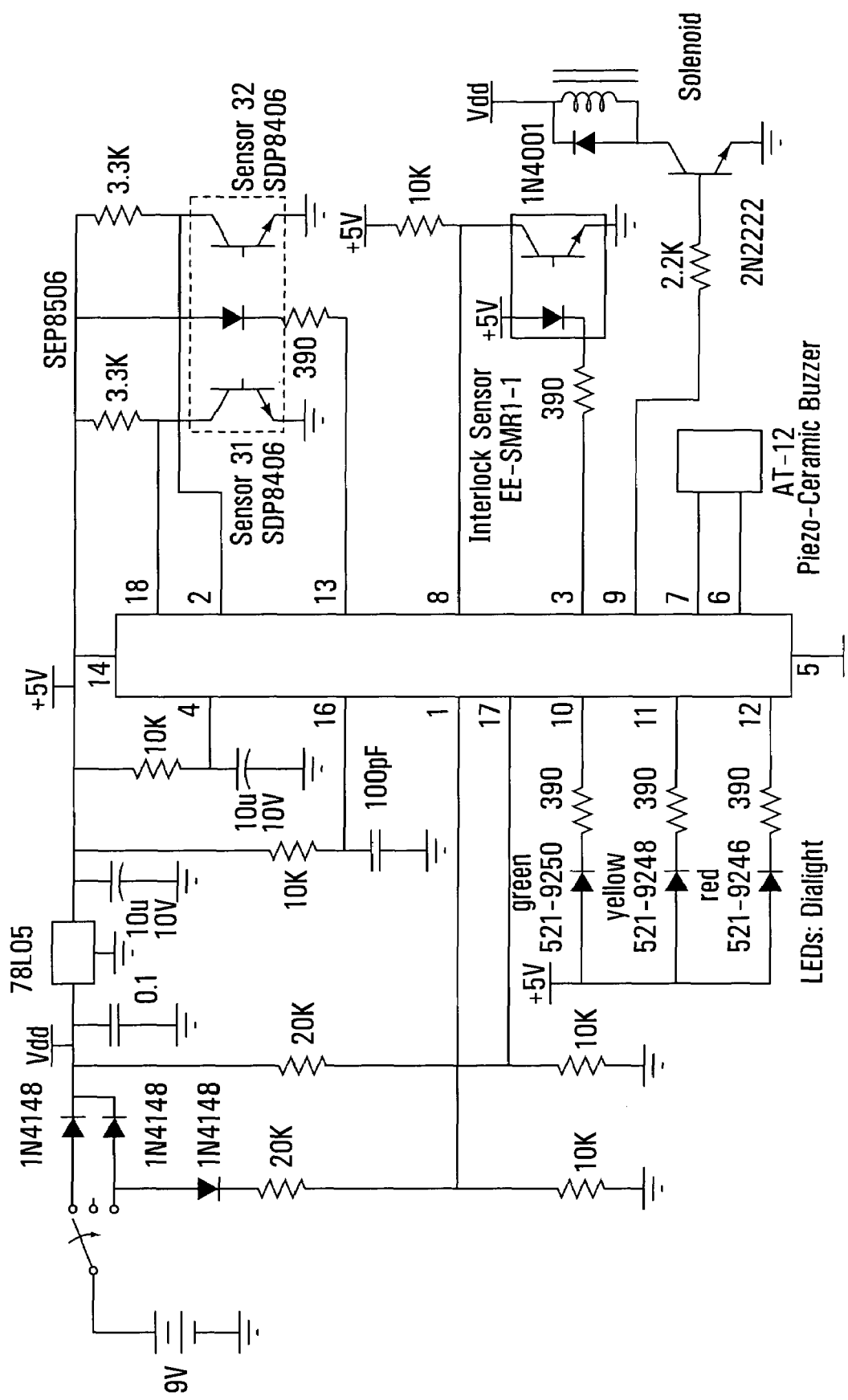
FIG. 2 is a circuit design.

A more detailed description of the electronics of the flowcheck now follows. The electronics is implemented with an embedded micro-controller to control excitation of the infrared emitter, read the values of sensor 31 and sensor 32 (see FIGS. 2 and 3), read the battery voltage, operate the indicator light-emitting diodes and the alarm beeper, and operate and verify operation of the fluid shutoff solenoid. The micro-processor includes a dedicated real-time operating system to implement the following task schedule:

every 1.3 milliseconds:
  toggle beeper—drive if beeper task enabled
every 10 milliseconds:
  beeper on/off—determine requested beeper, status
  indicator off—shut off indicators if required time elapsed
  solenoid trip task—energize solenoid until trip sensor asserted
every 0.1 seconds:
  detect fluid task—turn off emitter, read sensors 31 and 32, turn on emitter read sensors 31 and 32
  determine presence of fluid from readings—request alarm task if vial is empty alarm task request—red indicator LED
  shut off flow request—solenoid trip task if vial is empty
every 1 second:
  indicator on task—turn on indicators if requested (green "heartbeat", red and yellow indicators)
  read battery volts—read battery voltage, request low indication (yellow indicator) if voltage is less than 7 volts Optical Fluid Sensor Principles of Operation The system senses the presence of a transparent fluid (for example, saline, Ringers, glucose, etc.) in a cylindrical transparent vial which constitutes the drip chamber of an intravenous system. The presence of this fluid is sensed by determining the refractive properties of the vial using a doubly-differential optical strategy. This strategy also results in very low sensitivity to ambient light.

Determining Refraction of Filled and Empty Vials

Figure 3A:
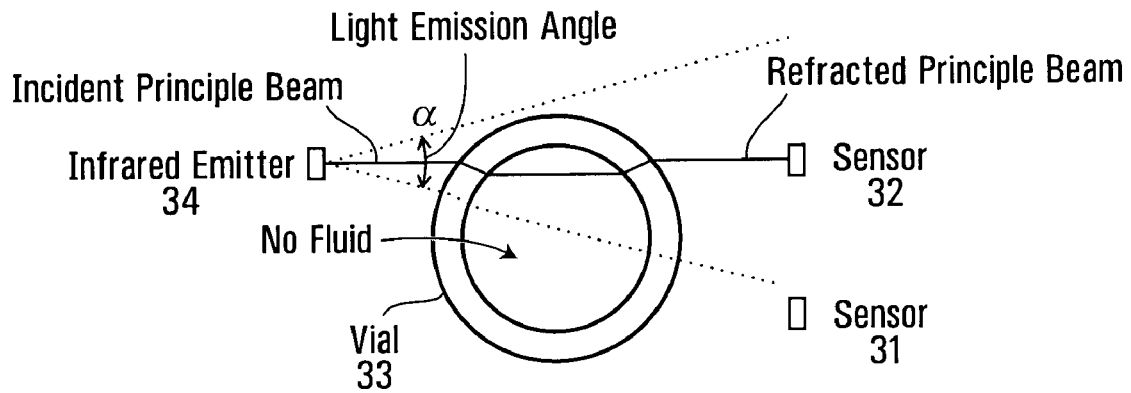
FIG. 3 is an emitter and sensor arrangement; and,
FIG. 4 is an exploded view of the device.
Figure 3B:
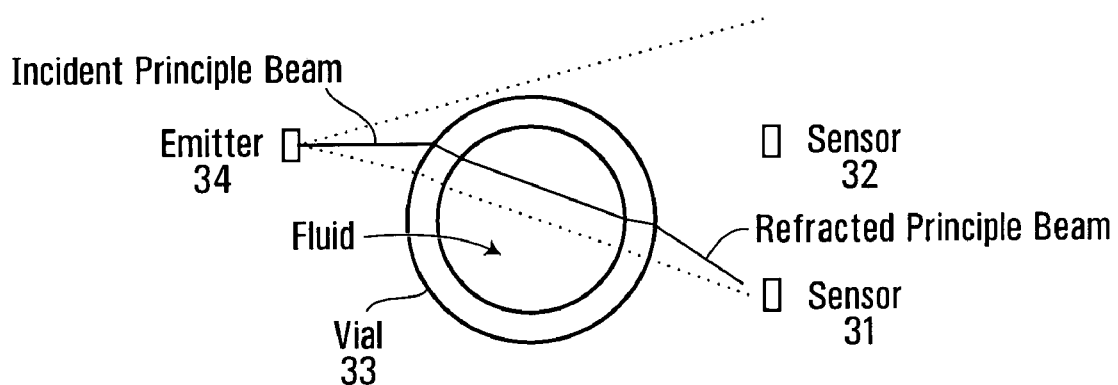

Optical determination of the refractive properties of the vial is performed by comparing the infrared light received by two sensors from a single infrared emitter. FIG. 3 shows a top view of the vial 33, the infrared emitter 34 and the two infrared sensors 31 and 32. The vial is shown in cross section. The two infrared sensors are positioned as shown on one side of the vial. The emitter is on the other side such that the emitter's principal emission direction forms a chord of both the inner and outer surfaces of the vial as shown. Alternatively, the same principle could be used by aligning both the infrared emitter and the two sensors on the same side of the vial and using a reflective surface (e.g. mirror) on the opposite side of the vial. This alternate arrangement would take advantage of the same refractive properties, while optimizing the configuration of the device.

The fundamental principle of operation is as follows. When the vial is empty, the principal beam (that beam emitted in the emitter's principal emission direction) is refracted twice by the air-vial interface both outside and inside the empty vial. Since the inside and outside walls of the vial are locally parallel, the light beam inside the vial is parallel to the incident principal beam. Similarly, the refracted beam is parallel to the beam inside the vial and therefore parallel with the incident beam. Sensor 32 is positioned so as to receive the majority of the refracted beam when the vial is empty. The small amount of beam energy which falls on sensor 31 is due to scattering and the highly divergent beam from the infrared emitter.

When the vial contains a clear fluid, the optical properties of the full vial are quite different. Since the refractive index of the fluid is much higher than for air and very similar to the refractive index of the vial material, the incident beam is refracted by the first air-vial interface, but is not refracted significantly by the vial-fluid interface. Thus, the light beam inside the vial is not at all parallel to the incident beam.

Proper positioning of the infrared emitter results in the beam in the filled vial meeting the vial wall near sensor 31, perpendicular to the vial wall. This beam will fall primarily on sensor 31, with very little beam energy received at sensor 32. The situation is shown in FIG. 3. The small amount of beam energy received at sensor 32 is due to scattering and the highly divergent beam from the infrared emitter.

Reducing Sensitivity to Ambient Light

An optical fluid sensor typically must operate in normal room illumination without extensive light baffles. To cancel any effect of ambient light, two readings are made for each sensor.

With the emitter off, each sensor is read to determine the amount of incident illumination. These readings are termed S1N and S2N. Then the emitter is turned on and two more readings, S1L and S2L, are made.

The absolute differences $$D1 = |S1N - S1L|$$

$$D2 = |S2N - S2L|$$

are formed and compared. These differences remove the effects of illumination of the two sensors by ambient light, since this light is not synchronous with the operation of the infrared emitter.

Fluid Detection

The vial is deemed to contain fluid if D1 is greater than D2, because this situation occurs when more light due to the infrared emitter is received at sensor 31 than sensor 32. If D2 is greater than D1, the vial is deemed to be empty since the incident principal beam does not undergo significant net refraction and so it falls largely on sensor 32.

Pinch-off Mechanism

A pinch-off mechanism is also described. It was designed to use the minimum number of parts, all of which are designed to be very simple, to achieve the goal of shutting off fluid flow (e.g. intravenous fluid) when actuated. The goal was to achieve complete shutoff with a simple, reliable and low-cost mechanism that consumes the minimum amount of energy. The pinch-off mechanism is suitable for use with the intravenous monitor described herein, but is not restricted to such use. The design of the pinch-off mechanism is described below, in a preferred embodiment, applied to intravenous tubing.

Figure 4:
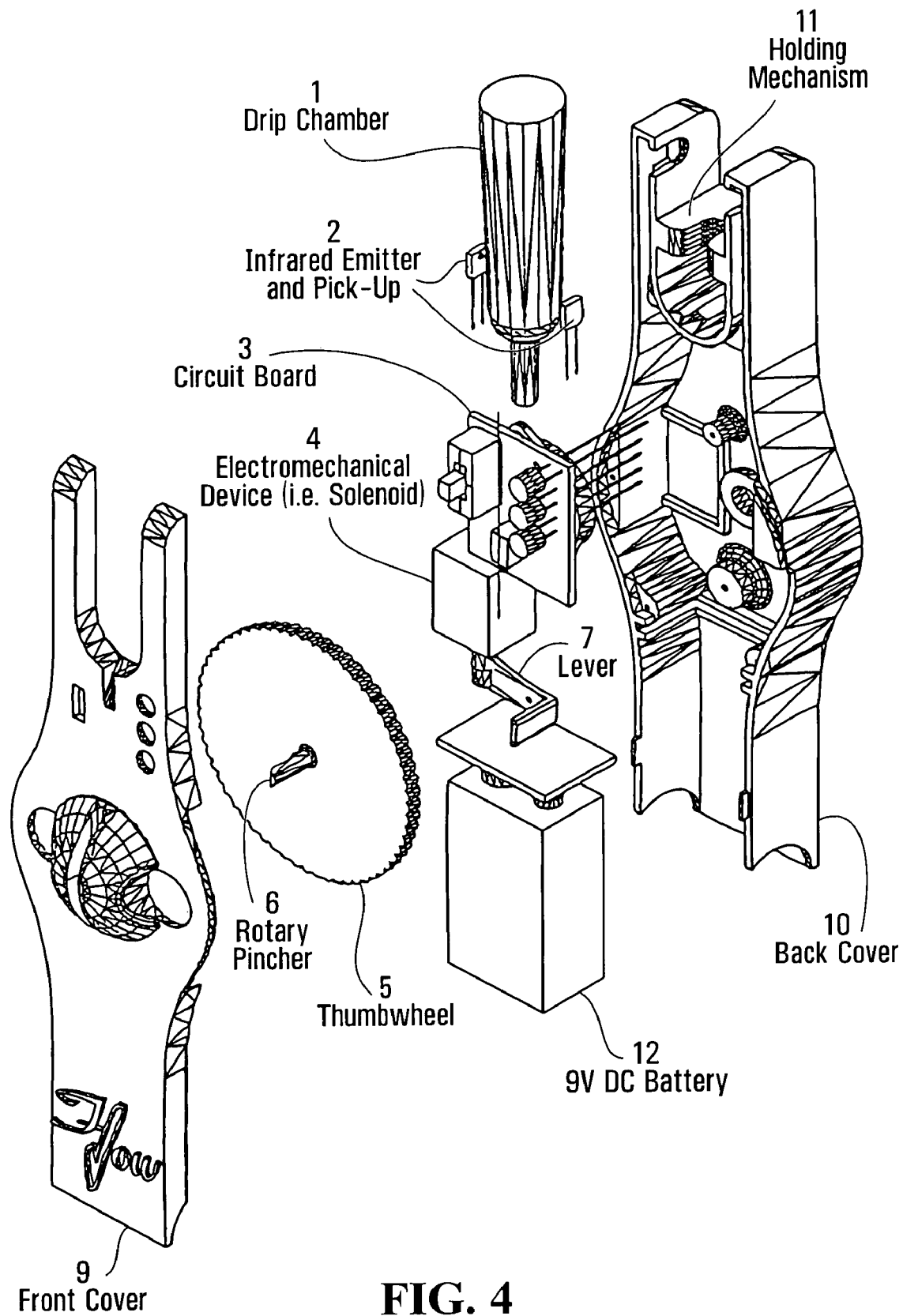

The mechanism consists of the following parts, with reference to FIGS. 1 and 4:

Thumbwheel 5 with integral rotary pincher 6, the torsion spring (not shown) that is cocked by the thumbwheel, the front cover 9 and specifically the narrow channel just off the center of the front of the domed part of the cover, the electromechanical device (solenoid by preference) 4, and the lever 7 that is spring-loaded into the 'loaded' position by a scissor spring (not shown). The mechanism is configured as follows:

1. The lever 7 is normally held by the scissor spring to cause it to engage a pawl molded on the back of the thumbwheel 5.
2. The electromechanical device 4 when actuated pulls on the lever 7 against the force of the scissor spring (not shown) so as to cause the lever to disengage from the pawl molded on the back of the thumbwheel 5.
3. The rotary pincher 6 consists of a half-cylinder that is integral to the thumbwheel 5 and that protrudes through a hole in the front cover 9 and capable of rotating in the front cover and is positioned such that at one position its flattened surface is flush with the side of the narrow channel that is just off center of the domed part of the front cover and that when rotated 90 degrees from this position it completely blocks the narrow channel.
4. A torsion spring is connected to the back cover 10 and the thumbwheel in such a manner that the thumbwheel can be rotated so as to store energy in the torsion spring, and that when released the thumbwheel will rotate to release the stored energy.

The mechanism performs as follows:

1. The electromagnetic device initially is not energized.
2. The user of the intravenous monitor cocks the mechanism by rotating the thumbwheel 5 90 degrees counter-clockwise when facing the front cover 9. This has the effect of storing energy in the torsion spring (not shown) and of rotating the rotary pincher 6 so that the narrow channel in the domed part of the front cover 9 is free of obstruction. When fully rotated, the scissor spring (not shown) on the lever 7 engages the pawl (not shown) on the back of the thumbwheel 5 so as to prevent the thumbwheel from rotating when released by the user of the invention.
3. The user of the intravenous monitor then inserts the intravenous tube into the narrow channel by stretching the tube slightly.
4. The user activates the intravenous monitor by turning it on.
5. When the infrared emitter and pickup 2 sense the absence of fluid in the drip chamber 1, the electronics on the circuit board 3 actuate the electromechanical device momentarily.
6. The electromechanical device then moves the lever 7 against the scissor spring (not shown) so that the lever no longer engages the pawl on the back of the thumbwheel.
7. The thumbwheel is now rotated through 90 degrees by the torsion spring (not shown) releasing the energy stored therein.
8. The rotary pincher 6 being integral to the thumbwheel 5 is also rotated through 90 degrees causing it to exert very high localized pressure on the intravenous tubing. This pressure is sufficiently high so as to completely occlude the tube.
9. To ensure actuation of the mechanism, the electronics on the circuit board 3 issues repeated, momentary actuation signals to the electromechanical device. This action stops at such time as the thumbwheel is released. The release of the thumbwheel is determined by an optical reflective sensor mounted so as to sense the presence of a small reflective surface (not shown) on the back of the thumbwheel 5. This provides a positive indication that guarantees release of the thumbwheel while minimizing energy consumption from the battery of the invention.

The design of the rotary actuator, the thumbwheel, the torsion spring and all other components has been optimized to provide reliable pinchoff of the intravenous tube at minimum cost and with minimum energy consumption.

It will be appreciated that the above description relates to the preferred embodiment by way of example only. Many variations on the invention will be obvious to those knowledgeable in the field, and such obvious variations are within the scope of the invention as described and claimed, whether or not expressly described.

The invention claimed is:

1. An optical fluid sensor device for detecting presence of fluid in a chamber, comprising:
    a radiation source;
    a first sensor disposed so that the chamber is situated between the radiation source and the first sensor, and disposed to receive a majority of radiation emitted from the radiation source when the portion of the chamber through which the emitted radiation passes contains no fluid;
    a second sensor disposed so that the chamber is situated between the radiation source and the second sensor, and disposed to receive a majority of radiation emitted from the radiation source when the portion of the chamber through which the emitted radiation passes contains fluid;
    a logic means for controlling the radiation source, and for detecting as a first signal an amount of radiation falling on the first sensor, and for detecting as a second signal an amount of radiation falling on the second sensor, and for comparing the first and second signals; and
    means for indicating when no fluid is detected in the chamber.

2. The optical fluid sensor device according to claim 1, wherein the indicating means is an audible alarm.

3. The optical fluid sensor device according to claim 1, wherein the indicating means is a visual alarm.

4. A pinch-off mechanism for occluding a conduit, comprising:
    a torsion spring;
    means for loading the torsion spring having a rotary pincher and a pawl; and
    an electromechanical device having a lever engaging the pawl,
    whereby, when activated, the electromechanical device disengages the lever from the pawl of the loading means releasing stored energy in the torsion spring which rotates the rotary pincher thereby applying pressure against the conduit thereby occluding it.

5. The pinch-off mechanism according to claim 4, wherein the electromechanical device is a solenoid.

6. A fluid monitoring device, comprising:
(i) an optical fluid sensor device for detecting presence of fluid in a chamber, comprising:
a radiation source;
a first sensor disposed so that the chamber is situated between the radiation source and the first sensor, and disposed to receive a majority of radiation emitted from the radiation source when the portion of the chamber through which the emitted radiation passes contains no fluid;
a second sensor disposed so that the chamber is situated between the radiation source and the second sensor, and disposed to receive a majority of radiation emitted from the radiation source when the portion of the chamber through which the emitted radiation passes contains fluid;
a logic means for controlling the radiation source, and for detecting as a first signal an amount of radiation falling on the first sensor, and for detecting as a second signal an amount of radiation falling on the second sensor, and for comparing the first and second signals; and
means for indicating when no fluid is detected in the chamber; and
(ii) a pinch-off mechanism for occluding a conduit, comprising:
a torsion spring;
means for loading the torsion spring having a rotary pincher and a pawl, wherein the pincher is located in a position on the conduit distal to the optical fluid sensor device in the direction of fluid flow; and
an electromechanical device having a lever engaging the pawl,
whereby, the indicating means activates the electromechanical device thereby disengaging the lever from the pawl of the loading means releasing stored energy in the torsion spring which rotates the rotary pincher thereby applying pressure against the conduit thereby occluding it.

7. A method for detecting presence of a fluid using an optical fluid sensor device as defined in claim 1, said method comprising:
activating the radiation source;
detecting radiation using the first sensor to produce a first signal and the second sensor to produce a second signal; and
comparing the first signal to the second signal to detect the presence of fluid in the chamber.

8. The method according to claim 7, further comprising:
detecting ambient radiation with the radiation source de-activated using the first sensor to produce a first reference signal and the second sensor to produce a second reference signal;
correcting the first signal by subtracting the first reference signal giving a corrected first signal;
correcting the second signal by subtracting the second reference signal giving a corrected second signal; and
comparing the corrected first signal to the corrected second signal to detect the presence of fluid in the chamber.

9. A method for monitoring administration of a fluid using the fluid monitoring device as defined in claim 6, said method comprising:
activating the radiation source;
detecting radiation using the first sensor to produce a first signal and the second sensor to produce a second signal;
comparing the first signal to the second signal to detect the presence of fluid in the chamber; and
activating the pinch-off mechanism to occlude the conduit when no fluid is present.

10. The method according to claim 9, further comprising:
detecting ambient radiation with the radiation source de-activated using the first sensor to produce a first reference signal and the second sensor to produce a second reference signal;
correcting the first signal by subtracting the first reference signal giving a corrected first signal;
correcting the second signal by subtracting the second reference signal giving a corrected second signal; and
comparing the corrected first signal to the corrected second signal to detect the presence of fluid in the chamber.

11. Use of an optical fluid sensor device as defined in claim 1 for detecting presence of a fluid in a flow system.

12. The use of claim 11, wherein the flow system is an intravenous system.

13. Use of a pinch-off mechanism as defined in claim 4 for occluding a conduit in a flow system.

14. The use of claim 13, wherein the flow system is an intravenous system.

* * * * *